United States Patent [19]

Kantor et al.

[11] Patent Number: 4,895,725

[45] Date of Patent: Jan. 23, 1990

[54] MICROENCAPSULATION OF FISH OIL

[75] Inventors: Martin L. Kantor, Mamaroneck; Solomon S. Steiner, Mt. Kisco; Howard M. Pack, Scarsdale, all of N.Y.

[73] Assignee: Clinical Technologies Associates, Inc., Elmsford, N.Y.

[21] Appl. No.: 177,498

[22] Filed: Apr. 4, 1988

Related U.S. Application Data

[63] Continuation-in-part of Ser. No. 88,651, Aug. 24, 1987.

[51] Int. Cl.$^4$ ................................................. A61K 9/66
[52] U.S. Cl. ..................................... 424/455; 264/4.1; 264/4.3; 264/4.33; 427/213.36; 424/451; 514/963
[58] Field of Search ............... 424/492, 451, 493, 455, 424/494, 107; 427/213.36; 264/4.1, 4.3, 4.33; 514/963

[56] References Cited

U.S. PATENT DOCUMENTS

| | | | |
|---|---|---|---|
| Re. 24,899 | 11/1960 | Green | 424/492 X |
| 3,567,650 | 3/1971 | Bakan | 252/316 |
| 3,956,172 | 5/1976 | Saeki et al. | 252/316 |
| 4,117,801 | 10/1978 | Dannelly et al. | 118/20 |
| 4,199,561 | 4/1980 | Roth et al. | 424/32 |
| 4,402,856 | 9/1983 | Schnoring et al. | 424/494 X |
| 4,460,563 | 7/1984 | Calanchi | 424/494 |
| 4,462,839 | 7/1984 | McGinley et al. | 106/198 |
| 4,473,620 | 9/1984 | Wu et al. | 428/402.24 |
| 4,518,433 | 5/1985 | McGinley et al. | 106/180 |
| 4,590,265 | 5/1986 | Bogan et al. | 536/63 |
| 4,766,012 | 8/1988 | Valenti | 424/494 X |

FOREIGN PATENT DOCUMENTS 1236885  9/1969  United Kingdom .

OTHER PUBLICATIONS

Madan and Shanbhag, "Cellulose Acetate Phthalate Microcapsules: Method of Preparation", *Communications, J. Pharm. Pharmac.*, 30, 65 (1978).

*Primary Examiner*—Thurman K. Page
*Attorney, Agent, or Firm*—Kilpatrick & Cody

[57] ABSTRACT

Microcapsules containing oil-based biologically active compounds which are stable over extended time periods for release of the encapsulated compound in the intestine. There are a number of biologically active compounds having an oil base which must be orally ingested in order to have a beneficial effect. An example of one such biologically active oil-based compound is a fish oil having a high content of polyunsaturated omega-3 fatty acids which has been demonstrated to reduce plasma levels of triglycerides, very low density lipoprotein, low density lipoproteins and cholesterol in normal and hyperlipidemic subjects. The disclosed microcapsules eliminate the unfortunate problems of the unpleasant taste and smell of the fish oil, as well as the aftertaste, particularly when ingested in large quantities, and provide a palatable and practical means of ingesting efficacious quantities of fish oil. In addition, the normal oxidation of polyunsaturated fatty acids is inhibited.

21 Claims, No Drawings

MICROENCAPSULATION OF FISH OIL

The present application is a continuation-in-part of U.S. Ser. No. 088,651, filed Aug. 24, 1987, by Howard M. Pack entitled "Palatable Fish Oil Compositions", describing a method for masking the odor and taste of fish oil so that large quantities may be ingested.

BACKGROUND OF THE INVENTION

This invention relates to tasteless, odorless, palatable fish oil-containing microcapsules.

As described in U.S. Ser. No. 088,651, the fish oil is encapsulated using conventional procedures within microcapsules formed of compounds such as gelatin and gelatin-acacia which are unstable in both the stomach and gastrointestinal tract. The microcapsules are then blended with a vegetable oil, such as peanut oil, that is immiscible with water. Although the microcapsules alone are unable to eliminate the odor and taste of the fish oil, the combination of the vegetable oil juxtaposed with the microcapsule enables one to completely mask the odor and taste of the oil.

Unfortunately, this method is limited to foods containing vegetable oils such as peanut butter, soybean products, or other similar materials. The oil is also released within the stomach, as well as the intestine, which can result in unpleasant side effects such as a fishy aftertaste or odor upon belching.

Studies have shown that fish oil which is high in polysaturated omega-3 fatty acids can substantially reduce levels of triglycerides, very low density lipoproteins, cholesterol and low density lipoprotein levels in normal and hyperlipidemic subjects. Unfortunately, the quantity of refined fish oil required to produce a substantial lowering of cholesterol and triglyceride levels in humans is often in excess of twenty grams per day. Even though the fish oil is dispensed in gelatin capsules of about one gram or more, quantities of twenty to thirty or more capsules per day are required to achieve a significant benefit from the oil. Further, a fishy taste and smell develop after ingestion, particularly after belching.

Other materials have been used to encapsulate oils. One method for encapsulation of oil is disclosed by British Pat. 1,236,885 to Fuji Photo Film Company, Ltd. This patent describes a method for preparing multiwall microcapsules containing oil where the wall film consists of a complex coacervate of gelatin and gum arabic. The microcapsules are dispersed in a water soluble high molecular film-forming material which is precipitated by addition to an aqueous solution containing hydroxyl, acid or basic groups and hardened by addition to a solution containing positive ions such as calcium. This is a complicated and inconvenient procedure, however, and does not prevent the aftertaste caused by belching up oil released in the stomach.

Although the compositions described in U.S. Ser. No. 088,651, filed August 24, 1987, by Howard M. Pack entitled "Palatable Fish Oil Compositions" is a substantial improvement over the commercially available gelatin fish oil-containing capsules, other compositions containing fish oil, or other oil-based compounds, which could be blended with a wide variety of food products as a pleasant means for consumption of the fish oil, are needed.

It is therefore an object of the present invention to provide compositions containing fish oil wherein the taste and smell is completely masked.

It is another object of the present invention to provide compositions containing fish oil which can be incorporated into a variety of solid and aqueous-based food products for easier ingestion of quantities sufficiently large to result in the desired effect.

It is a further object of the present invention to provide fish oil compositions which release the fish oil in the lower gastrointestinal tract rather than the stomach.

It is a still further object of the present invention to provide a method and means for encapsulating other bioactive oils for oral delivery to the lower gastrointestinal tract.

SUMMARY OF THE INVENTION

Fish oil-containing microcapsules suitable for incorporation into a variety of aqueous based and dry food products such as gelatin, orange juice and yogurt are prepared by encapsulating fish oil within an enteric coating such as ethyl cellulose.

The microcapsule are formulated from an emulsion of fish oil and enteric coating suspended in a basic solution, preferably a 25% suspension of ethyl cellulose in ammonium hydroxide. The emulsion is atomized into an acidic solution using an inert gas such as nitrogen or argon. The resulting microcapsules are filtered out of the acidic solution, washed with water and a surfactant and dried. The conditions under which the emulsion is atomized determines the particle size, which can range from about 0.1 to 500 microns, preferably between about 0.5 to 100 microns.

The fish oil microcapsules are odorless, tasteless, and have a smooth, creamy consistency when made under the preferred conditions. The encapsulated fish oil is stable both at room temperature and at 4° C., in the presence of light, and when incorporated into a variety of food products. The enteric coating disintegrates under neutral and basic conditions, as when the microcapsules are ingested and reach the intestine.

DETAILED DESCRIPTION OF THE INVENTION

The microencapsulated fish oil of the present invention was developed in response to a need for a stable, odorless, tasteless composition suitable for incorporation into a food product. In the absence of the enteric coating made using the below-described method, or the method described in U.S. Ser. No. 088,651 filed Aug. 24, 1987, the fish oil has a strong odor and taste which is particularly objectionable when the fish oil is ingested in the sufficiently high quantities required to produce a beneficial effect, i.e., a substantial reduction in plasma triglyceride, low density lipoprotein levels and cholesterol levels. These quantities appear to be in the range of between 10 grams per day up to as much as 30 grams of fish oil per day.

The present invention not only overcomes the problems of the offensive odor and taste of the fish oil, it helps reduce oxidation of the polyunsaturated fatty acids and delays release to a point where maximum absorption will occur. It also results in release of the fish oil below the pylorus in the upper portion of the intestine, allowing for efficient absorption without the unpleasant side effects such as regurgitation of the oil or fishy aftertaste or breath.

In addition to fish oil, a variety of oil-based bioactive materials can be encapsulated and ingested according to the method of microcapsulation of the present invention. For example, other fish oils such as cod liver oil, mineral oil, oil-soluble vitamins and drugs which are delivered in an oil base, can be incorporated into the microcapsules. An example of a drug which is normally delivered orally in an oil base within a capsule is cyclosporin, an immunosuppressant which must be taken on a long-term basis to avoid graft rejection or to treat other autoimmune disease.

In the present invention, an enteric coating such as ethyl cellulose is preferred for forming an emulsion with the oil. Other useful cellulose derivatives include cellulose acetate trimellitate and cellulose acetate phthalate. A number of enteric coatings have been FDA approved. These materials are soluble only in organic or basic aqueous solutions, not in oil or acidic solutions. An enteric coating is defined as a polymeric material which is insoluble at acidic pH but soluble at a pH greater than about 5 -5.5 or physiological pH. For example, cellulose acetate trimellitate dissolves in an aqueous solution of pH greater than about 5.5.

Example 1

Preparation of Microcapsules Within an Alginatecellulose acetate capsule

Microcapsules having diameters of between 2 microns and 1 millimeter were prepared from an emulsion of alginate and oil precipitated by addition to a solution containing calcium. The oil-containing microcapsules were then resuspended in a basic solution of an enteric coating, cellulose acetate phthalate, which was precipitated around the alginate-walled microcapsules by addition of the cellulose acetate phthalate in a basic solution into an acid solution.

Although the microcapsules containing the fish oil initially did not have either an unpleasant taste or odor, these microcapsules were not stable over time.

EXAMPLE 2

Encapsulation of Fish Oil Within an Oil-Insoluble Enteric Coating

As emulsion of 20 parts commercially obtained fish oil, such as fish oil rich in polyunsaturated omega-3 fatty acids sold under the trademark MAX EPA by Seven Seas Health Care Ltd., Marfleet, Hull, U.K. or fish oil sold under the trademark SAN OMEGA by Nippon Oil & Fats Co., 10-1 Yuraku-cho, 1 Chome, Chiyoda-ku, Tokyo, Japan, and 80 parts of a 25% suspension of ethyl cellulose in ammonium hydroxide was prepared under nitrogen. The emulsion was atomized using a nitrogen stream into a stirred solution of glacial acetic acid in water (50:1000). Oil-containing microcapsules were formed in the acetic acid solution. These were filtered, washed extensively with water, washed with 0.5% Tween 20, and washed extensively with water. The microcapsules were dried.

These microcapsules were stable both at room temperature in light and at 4° C. for an extended period of time. In contrast to the microcapsules formed in Example 1 which turned rancid after about three days, these microcapsules were still stable after more than one month.

Variations to this method include alteration of the ratio of oil to enteric coating, chemical formula of the enteric coating, type and pressure of inert gas, particle size, type and relative volume of acidic solution used for precipitation, and additives to either the emulsion or acidic solution.

Although the preferred ratio of oil to ethyl cellulose is 1:1, a range of ratios of fish oil to ethyl cellulose of from approximately 1:0.5 to 1:10 could be used.

Although glacial acetic acid is preferred, any other acid FDA approved for ingestion such as citric acid, lactic acid, malic acid, ascorbic acid, or phosphoric acid could be utilized. The relative volume of the enteric coating suspension to the acidic solution may be adjusted as required to obtain the desired size and quantity of microcapsules. In general, the volume should be sufficient to provide adequate stirring and to provide a clear surface for contacting the enteric coating-fish oil emulsion onto. A dispersing agent, such as starch, silica or kaolin, may be added to the enteric coating-oil emulsion or suspension, before or after atomizing.

The preferred temperature for the procedure is room temperature but the procedure may be carried out at a temperature generally between 0° C. and 50° C., low enough not to cause oxidation of the oil or loss of biological activity and high enough that the oil does not congeal.

The particle size is adjusted by varying the nozzle diameter and pressure of the atomizer. Inert gases such as argon or helium can be substituted for nitrogen. In the above example, a modified air brush was used to atomize the oil-enteric coating suspension. Particle size can vary between 0.1 and about 500 microns. The smaller size particles have a creamier consistency but lower loading capacity than the larger diameter particles. For example, particles having diameters of between about 0.1 and 1 micron have a consistency like butter. Microcapsules having a diameter of approximately 100 microns have a consistency of approximately that of cream cheese. In contrast, particles of greater than approximately 250 microns have a grainy texture. The preferred range is generally between about 0.5 and 250 microns.

Apparatus for forming and removing the microcapsules in the acidic solution are known to those skilled in the art, as are other methods of removing and washing the microcapsules.

EXAMPLE 3

Preparation of Fish Oil Microcapsule-Containing Food

Capsules prepared according to Example 1 were not stable over a period of more than three days and when incorporated into a variety of foods were found to have an objectionable taste and odor. In contrast, the microcapsules formed in Example 2 were mixed with flavored gelatin, orange juice, agar gel flavored with raspberry syrup and citric acid, yogurt and peanut butter, without subsequent degradation of the enteric coating. No objectionable taste or odor was observed over a period of more than three weeks.

In general, these microcapsules can be incorporated into any aqueous, oil-based or dry food product having a pH of about less than 7 or less than the pH at which the enteric coating dissolves. Particle size can be varied to produce the desired consistency.

Modifications and variations of the present invention, a method for forming fish oil-containing microcapsules having no objectionable taste or odor for subsequent incorporation into foods, will be obvious to those skilled in the art from the foregoing detailed description of the invention. Such modifications and variations are intended to come within the scope of the following claims:

We claim:

1. Palatable microcapsules comprising a biologically active material and an oxidizable oil having a strong odor and taste encapsulated within a non-oil soluble enteric coating to form microcapsules having no taste or smell derived from the oil, said coating formed by preparing an emulsion of an oil-based biologically active compound and a non-oil soluble enteric coating in a basic solution, atomizing the emulsion into an acidic aqueous solution, and separating the precipitated microcapsules from the acidic aqueous solution.

2. The microcapsules of claim 1 wherein said oil-based biologically active material is fish oil containing polyunsaturated omega-3 fatty acids.

3. The microcapsules of claim 1 wherein said enteric coating is a cellulose derivative.

4. The microcapsules of claim 3 wherein said enteric coating is selected from the group consisting of ethyl cellulose, cellulose acetate trimellitate, and cellulose acetate phthalate.

5. The microcapsules of claim 1 wherein said microcapsules have a diameter of between approximately 0.1 and 500 microns.

6. The microcapsules of claim 5 wherein said microcapsules have a diameter of between approximately 0.5 and 250 microns.

7. The microcapsules of claim 1 wherein the enteric coating and the biologically active oil-based compound are in a ratio of between approximately 1:0.5 to 1:10.

8. The microcapsules of claim 1 wherein said microcapsules are formed by preparing an emulsion of the oil-based biologically active compound and enteric coating in a basic aqueous solution and atomizing the emulsion into an acidic solution.

9. The microcapsules of claim 1 blended with an edible food product having a pH of less than the pH at which the enteric coating dissolves.

10. A method for preparing edible microcapsules containing a biologically active compound and an oxidizable oil having a strong odor and taste comprising preparing an emulsion of an oil-based biologically active compound and a non-oil soluble enteric coating in a basic solution, atomizing the emulsion into an acidic aqueous solution to precipitate the enteric coating around the oil-based biologically active compound to form microcapsules having no taste or smell derived from the oil, and removing the precipitated microcapsules from the acidic solution.

11. The method of claim 10 wherein the enteric coating is a derivative of cellulose.

12. The method of claim 10 wherein the enteric coating is selected from the group consisting of ethyl cellulose, cellulose acetate trimellitate, and cellulose acetate phthalate.

13. The method of claim 11 wherein the enteric coating is suspended in an ammonium hydroxide solution.

14. The method of claim 10 wherein the enteric coating and the biologically active oil-based compound are in a ratio of between approximately 1:0.5 and 1:10.

15. The method of claim 10 wherein the emulsion is prepared and precipitated under an inert gas atmosphere.

16. The method of claim 10 further comprising washing the microcapsules with a surfactant.

17. The method of claim 10 further comprising mixing the microcapsules with a food having a pH less than the pH at which the enteric coating dissolves.

18. The method of claim 10 wherein the oil-based biologically active compound is fish oil containing polyunsaturated omega-3 fatty acids.

19. The method of claim 10 wherein the emulsion comprises fish oil and a 25% suspension of ethyl cellulose in ammonium hydroxide.

20. The method of claim 10 wherein the emulsion is precipitated to form microcapsules having a diameter of between approximately 0.1 and 500 microns.

21. The method of claim 10 wherein the emulsion is precipitated in an acid selected from the group consisting of acetic acid, phosphoric acid, lactic acid, ascorbic acid, malic acid, and citric acid.

* * * * *